United States Patent [19]

Magram

[11] Patent Number: 5,634,894
[45] Date of Patent: Jun. 3, 1997

[54] ANTISIPHONING VALVE

[75] Inventor: Gary Magram, Greenville, Del.

[73] Assignee: The Nemours Foundation, Wilmington, Del.

[21] Appl. No.: 566,146

[22] Filed: Dec. 1, 1995

[51] Int. Cl.$^6$ ..................................... A61M 5/00
[52] U.S. Cl. ..................................... 604/10; 604/9
[58] Field of Search .................. 604/7–10; 137/38, 137/44

[56] References Cited

U.S. PATENT DOCUMENTS

| | | | |
|---|---|---|---|
| 2,703,582 | 3/1955 | Stepanian | 137/38 |
| 2,927,592 | 3/1960 | Ferre, Sr. | 137/38 |
| 3,889,687 | 6/1975 | Harris et al. | 128/350 |
| 4,524,794 | 6/1985 | Haines | 137/202 |
| 4,540,400 | 9/1985 | Hooven | 604/9 |
| 4,551,128 | 11/1985 | Hakim et a. | 604/9 |
| 4,606,365 | 8/1986 | Siposs | 604/9 |
| 4,621,654 | 11/1986 | Holter | 137/38 |
| 4,673,384 | 6/1987 | Marion | 604/10 |
| 4,729,762 | 3/1988 | Doumenis | 604/10 |
| 4,776,838 | 10/1988 | Sainte-Rose et al. | 604/9 |
| 4,867,741 | 9/1989 | Portnoy | 604/10 |
| 4,883,456 | 11/1989 | Holter | 604/9 |
| 5,042,974 | 8/1991 | Agarwal | 604/9 |
| 5,069,663 | 12/1991 | Sussman | 604/9 |
| 5,336,166 | 8/1994 | Sierra | 604/9 |
| 5,368,556 | 11/1994 | Lecuyer | 604/8 |

*Primary Examiner*—John G. Weiss
*Assistant Examiner*—Ki Yong O
*Attorney, Agent, or Firm*—Jeffrey C. Lew

[57] ABSTRACT

A valve for preventing excessive cerebrospinal fluid flow in ventriculoperitoneal shunt, known as "siphoning", which occurs when a patient rapidly moves from a recumbent to an upright position, is described. The valve includes at least one valve unit containing within a cerebrospinal fluid (CSF)-filled cavity, a freely moveable float which is buoyant in CSF. The valve is subcutaneously implanted in the patient in an upright orientation in which the entrance port of the valve unit is elevated higher than the cavity while the patient is upright. In this orientation, the float rises to the top of the CSF-filled cavity where it seals against a seat of the entrance port. The float thus stops flow until intracranial pressure sufficiently exceeds the buoyant force. The casing generally has a contoured sectional profile. When the patient reclines, the valve orients so that the float rises to a high region of the casing which is away from the entrance seat thereby allowing CSF to flow through. The contour of the casing is selected to increase hydrodynamic force on the float in the direction of flow when flow rate increases. This causes the float to contact a seat of the valve unit exit port when flow exceeds a predetermined amount. The novel valve thus provides the capability to prevent excessive drainage even when the patient is recumbent, for example, caused by coughing or sneezing.

9 Claims, 4 Drawing Sheets

ANTISIPHONING VALVE

FIELD F THE INVENTION

This invention relates to ventriculoperitoneal shunts, and more specifically, to a valve to moderate cerebrospinal fluid flow when the patient changes between recumbent and upright positions.

BACKGROUND OF THE INVENTION

Treatment of certain medical conditions and diseases such as hydrocephalus frequently includes implanting a subcutaneous ventriculoperitoneal (VP) shunt to drain cerebrospinal fluid (CSF) from a ventricle of the brain to a receiving cavity, such as the heart or peritoneum. A VP shunt typically includes a catheter which extends from the ventricle, through a burr hole in the skull located behind the ear, and along the side of the body to the abdomen.

Early VP shunts exhibited a performance characteristic known as "siphoning" which refers to surging of CSF drainage when the patient changes from a recumbent to a sitting or standing position. Siphoning is caused by the rapid increase in hydrostatic pressure differential in the catheter due to the sudden change in height of the head above the abdomen. In addition to temporary discomfort, excessive CSF drainage might cause other adverse consequences, for example, distention of the brain, or rupture of the blood vessels leading to potentially serious brain hematoma.

To eliminate siphoning, VP shunts sometimes incorporate an antisiphoning valve which continuously senses the patient's attitude (i.e., horizontal-to-vertical orientation) and automatically moderates flow when the patient moves to an upright position. A weighted ball check valve is the operative mechanism frequently used in conventional antisiphoning valves. Generally in such valves, one or more spherical balls which are more dense than CSF reside within a hollow cavity of an elongated housing with a seat at the CSF inlet end. The antisiphoning valve is implanted so that the housing is horizontally oriented when the patient lies down. In the horizontal orientation, the balls can roll away from the seat, thus allowing CSF to pass through the valve. When the patient sits or stands, the housing orients vertically with the seat at the bottom. The balls sink toward the seat, thereby stopping flow until the aggregate intracranial and hydrostatic pressures of fluid in the catheter exceeds the force exerted by the weight of the balls against the seat.

A patient also is susceptible to experience CSF surging while recumbent. When a patient coughs or sneezes, for example, which of course can occur while lying down, intracranial pressure temporarily increases and produces high flow through the catheter. A weighted ball valve does not stop flow while the patient is recumbent because the ball can roll away from the seat. Therefore, a conventional weighted ball, antisiphoning valve is not able to protect against CSF surges while the patient is in a recumbent attitude.

In a weighted ball antisiphoning valve the flow enters from the bottom to assure that the ball will sink toward the seat in the upright orientation. Bottom entry causes the fluid to follow an S-shaped path from the brain to the abdomen. That is, fluid must travel downward to descend below the bottom seat, then upward past the seat and ball, and downward again to its ultimate destination. The shunt valve disclosed in U.S. Pat. No. 5,042,974 exemplifies such S-shaped fluid flow path of a bottom entry, weighted ball, antisiphoning valve. To accommodate the S-shaped path, conventional antisiphoning valves are bulky. Due to its size, the valve tends to remain in fixed position when implanted in the patient. As the patient grows, the distance between the ends of the catheter and the valve increase which stresses the elastic tubing normally used in VP shunts. This stress increases the probability that the tubing will disconnect from the shunt components and require surgical intervention to correct.

It is an object of the present invention to provide a streamlined, antisiphoning valve in which CSF flows straight through in a non-meandering path. Such a valve can have a smaller cross section than a conventional valve of equal capacity. The small cross section promotes the ability of the valve to move in the axial direction of the catheter within the body of the patient to relieve stress caused by the patient's growth.

It is another object of this invention to provide an attitude responsive, antisiphoning valve which can reduce surging fluid drainage even when the patient is recumbent.

SUMMARY OF THE INVENTION

Accordingly, there is provided an antisiphoning valve for a ventriculoperitoneal shunt comprising:

- a hollow body defining at least one internal fluid chamber having a chamber wall;
- an outlet port on the body to connect the antisiphoning valve in fluid communication between the at least one chamber and a discharge cannula;
- an inlet port on the body distant from the outlet port to connect the antisiphoning valve in fluid communication between the at least one chamber and a supply cannula;
- at least one freely moving float within each chamber, the at least one freely moving float being buoyant in cerebrospinal fluid; and
- a first seat on the chamber wall proximate to the inlet port adapted to mate with the at least one freely moving float to stop cerebrospinal fluid flow when the antisiphoning valve in use is oriented in an upright attitude wherein the inlet port is elevated higher than the at least one chamber thereby causing cerebrospinal fluid in the chamber to buoy up the float to mate with the seat.

The present invention also provides an antisiphoning valve as just described and further comprising a second seat on the chamber wall distant from the first seat adapted to mate with the at least one freely moving float to stop cerebrospinal fluid flow when the at least one freely moving float mates with the second seat.

There is further provided a method of shunting cerebrospinal fluid from a ventricle of the brain to a receiving cavity which incorporates using the above-described antisiphoning valve to prevent excessive fluid drainage when a patient moves from a recumbent to an upright attitude.

3

Figure 6:
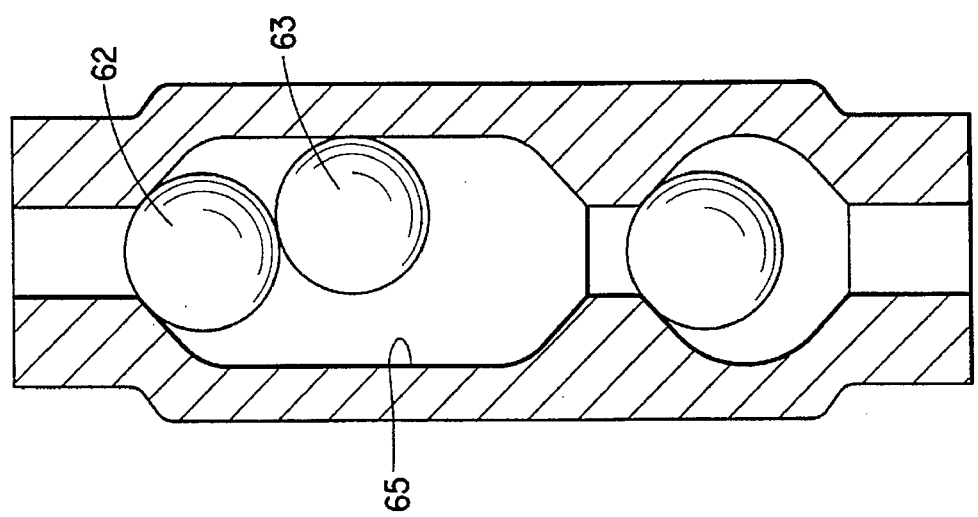

FIG. 6 is a section view of a different embodiment of an antisiphoning valve according to the present invention, wherein a valve unit includes more than a single float.

Figure 7:
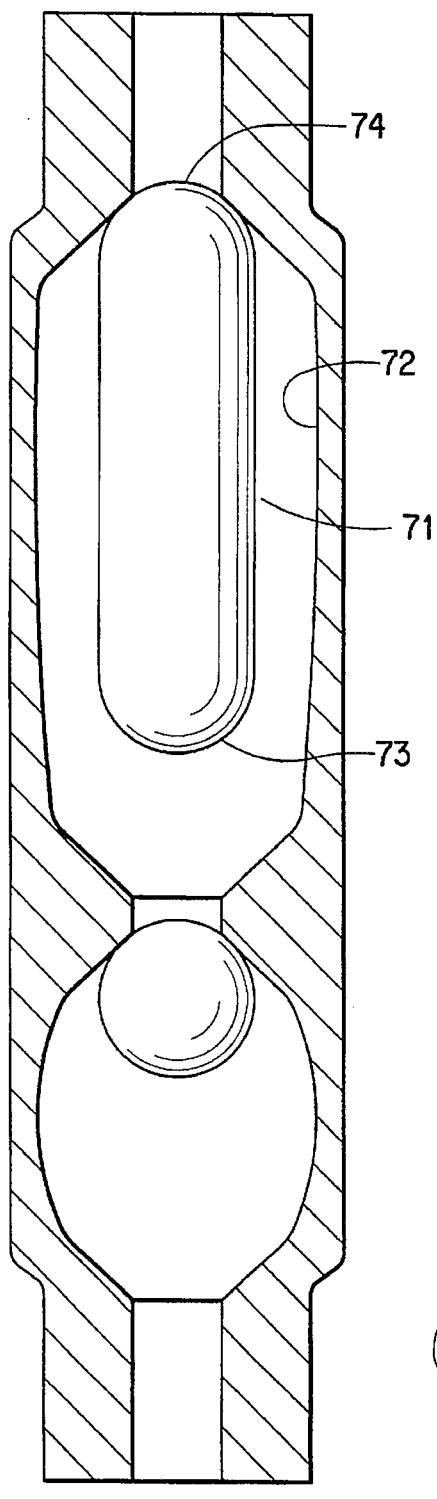

FIG. 7 is a section view of a different embodiment of an antisiphoning valve according to the present invention, wherein a float is torpedo-shaped.

Figure 8:
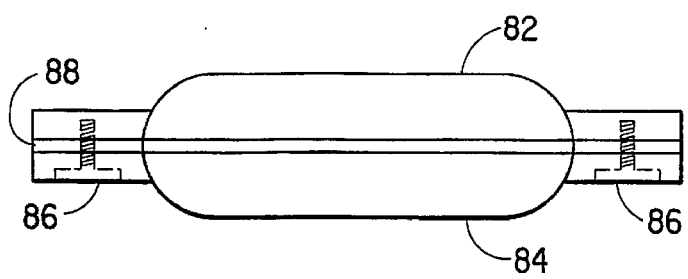

FIG. 8 is a side elevation view of an antisiphoning valve according to the present invention.

DETAILED DESCRIPTION

Figure 1:
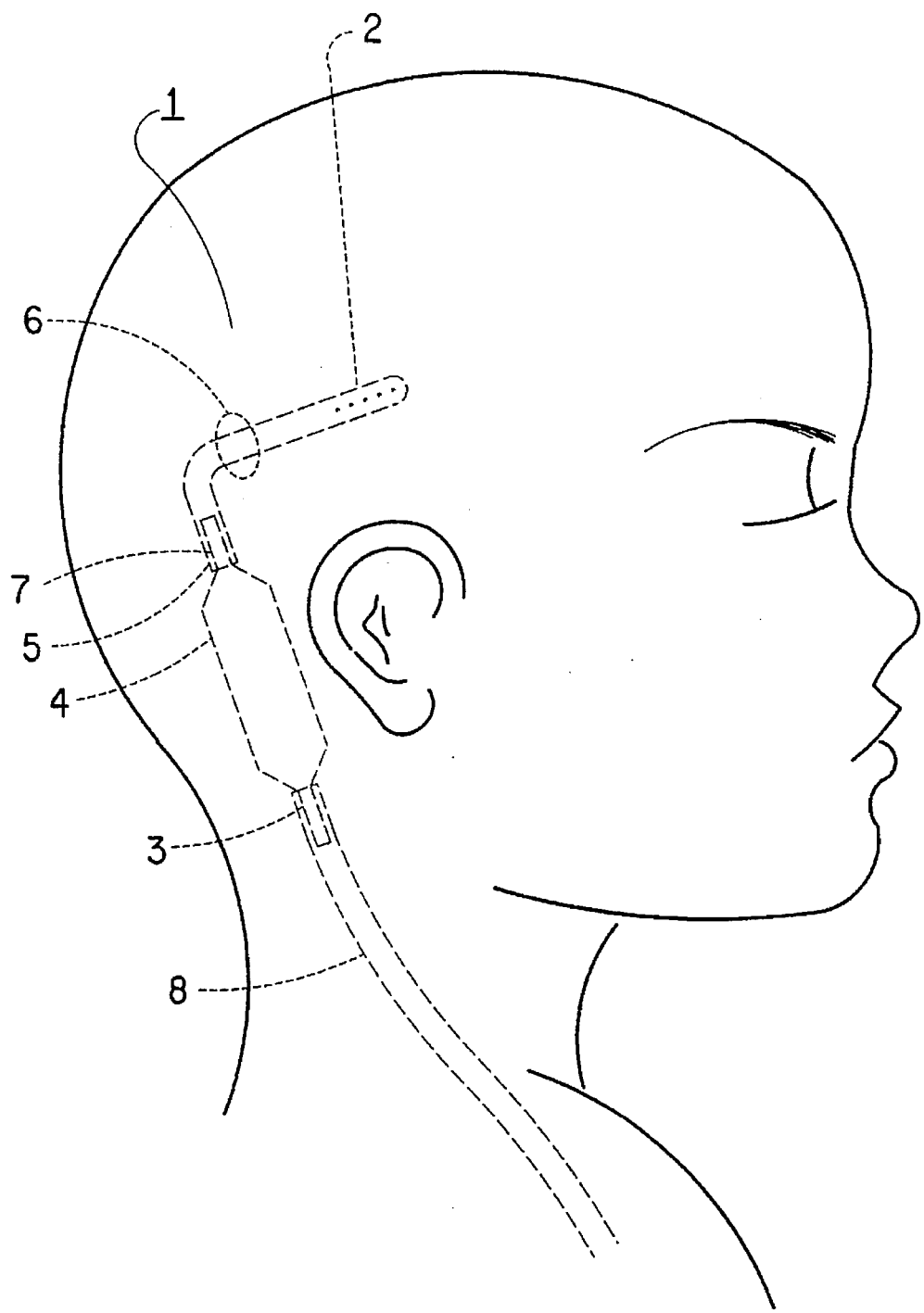
FIG. 1 is a diagram of a typical ventriculoperitoneal shunt.

FIG. 1 illustrates a ventriculoperitoneal (VP) shunt 1 which incorporates the antisiphoning valve of the present invention. The shunt includes a supply cannula 2 which extends through a burr hole 6 in the skull into a ventricle of the brain, not shown. The proximal end 5 of the cannula is connected to a tubular shaped inlet port 7 of antisiphoning valve 4. Tubular shaped outlet port 3 of the valve provides connection to discharge cannula 8 leading to a receiving cavity, such as the peritoneum, in the abdomen, not shown. The antisiphoning valve body is elongated and contains an internal valve unit, not shown, which aligns with the longitudinal axis of the valve such that the entrance port and the exit port of the valve unit are proximate and distant from the inlet port, respectively, as will be explained in greater detail, below. FIG. 1 thus shows the proper orientation of the implanted antisiphoning valve 4 to achieve intended performance. That is, the longitudinal axis of the antisiphoning valve is oriented in the body to align the entrance port to the top of the valve unit when the patient is upright and away from the top of the valve unit when the patient is recumbent.

Figure 3:
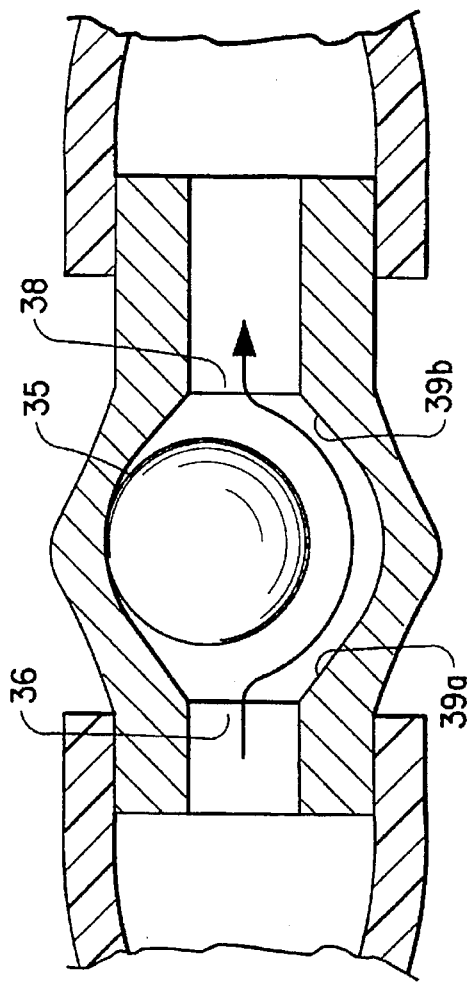
FIG. 3 is a section view of the antisiphoning valve of FIG. 2 shown in a horizontal orientation.
Figure 4:
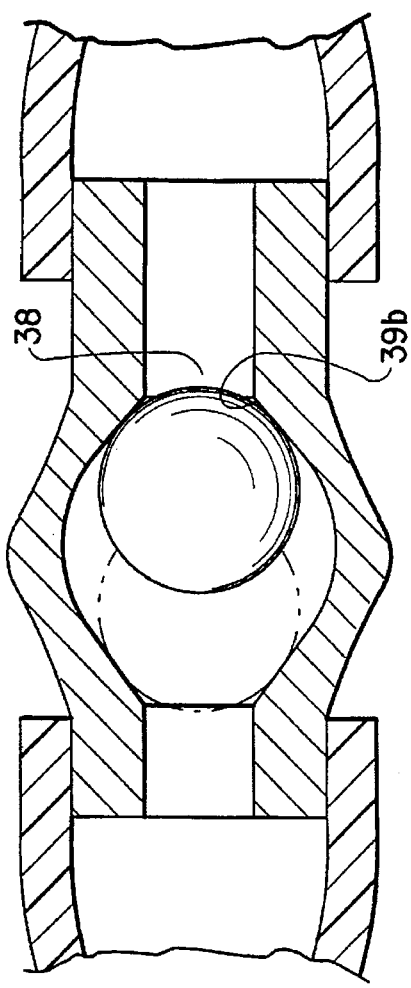
FIG. 4 is a section view of the antisiphoning valve of FIG. 3 shown during a fluid surge condition.
Figure 2:
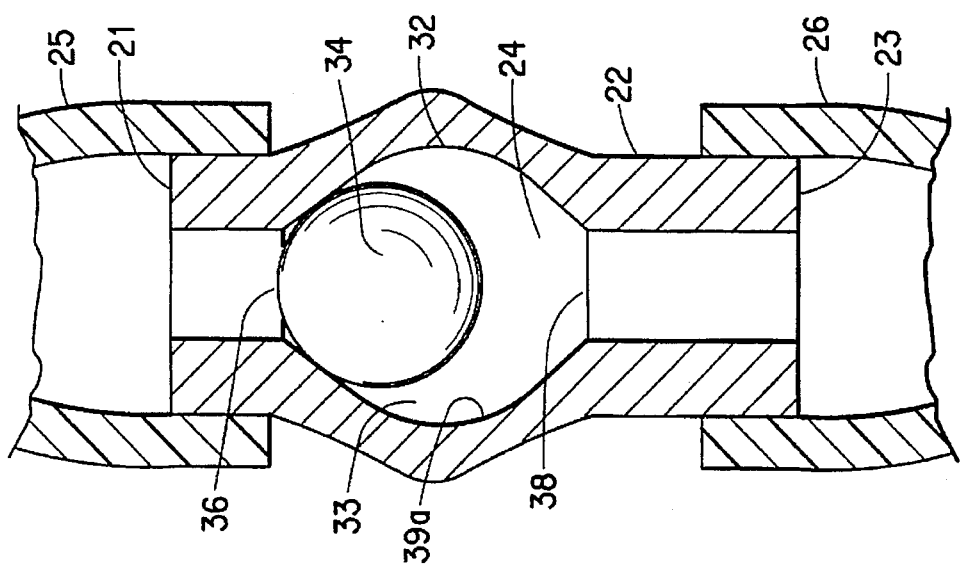
FIG. 2 is a section view of an antisiphoning valve according to the present invention in a vertical orientation.

A basic embodiment of the antisiphoning valve of this invention is shown in FIGS. 2–4. Like elements in the figures are provided with the same reference designations. The valve is shown as oriented in a patient in an upright position in FIG. 2 and in a recumbent position in FIGS. 3 and 4. The antisiphoning valve includes an elongated hollow body 22 which defines an internal fluid chamber 24. The body preferably has a generally cylindrical exterior shape, however, the cross section need not be circular or uniform across the length of the valve. The valve includes inlet port 21 and outlet port 23 which are tubular extensions of the body useful for connecting the valve to supply and discharge cannulae, 25 and 26, respectively, by inserting the port into the lumen of the cannula. The cannulae in VP shunts are normally circular cross section, soft, elastomeric tubes. The outer dimensions of the inlet and outlet ports are selected to be slightly larger than the inner diameter of the cannula which causes the cannula wall to expand when the port is inserted in the lumen. This provides a liquid tight seal between the inside surface of the cannula and the outside surface of the port.

The illustrated inlet and outlet ports are generally cylindrical, with a circular cross section of constant outer diameter, however, other shapes are contemplated. For example, the port can be frustoconical or it can have one or more circumferential, outwardly radiating sealing ridges to further assure a snug fit between the cannula and the port. The sealing ridges can be the same or different size. For example, size of the sealing ridge can vary with distance from the end of the port. More specifically, the sealing ridge near the end of the port can have the smallest outer diameter and the ridge furthest from the end can have the largest outer diameter. The peaks of the ridges can be rounded or they may have a sharp-tipped, frustoconical cross section. Such sharp-tipped ridges define teeth which bite into the cannula wall which increases the resistance of the cannula to accidentally disconnect from the port. Mechanical means for clamping the cannula to the port, such as ligated sutures, can be used to increase resistance of the cannula to disconnect.

The basic antisiphoning valve has a single valve unit which includes a contoured casing 32 and a float 34. The casing defines a concave, generally oval cavity 33 that surrounds the float and which normally is filled with cerebrospinal fluid in service. The casing has an entrance port 36 through which fluid enters the cavity. Similarly, the casing has an exit port 38 which leads to the opening of the outlet port 23. Preferably, float 34 is spherical. The dimensions of the casing are sufficiently larger than those of the float to permit the float to move freely within the cavity. However, the entrance and exit port opening cross section dimensions are smaller than the float to confine the float within the cavity.

The float material has a lower specific gravity than CSF, and therefore, it floats in the fluid. The float can be solid, low density material, such as low density or ultra low density polyolefin plastic. It can also be a composite of a shell and core of different materials, provided that the overall specific gravity is less than that of CSF. The float also can be hollow. Preferably, the float and cavity surfaces should be suitably lubricious and biocompatible that biological matter and debris which may be suspended in the fluid do not appreciably adhere to the surfaces and occlude the fluid passage way. The surfaces may be coated with a layer of nonadhesive material, such as polytetrafluoroethylene.

The entrance port meets the cavity in a cross section, preferably circular, adapted to form a liquid tight seat for the float. More preferably, the seat, 39a, is frustoconical. Due to the low specific gravity of the float, buoyant force causes the float to rise to the top of the cavity, as shown in FIG. 2. Thus CSF inlet flow is stopped until hydrostatic pressure exerted from above the valve, increases sufficiently to overcome the buoyant force exerted by the float against the seat. When this condition occurs, the float moves downward to permit CSF to flow to the outlet port. As fluid drains from the ventricle, intracranial pressure decreases, which causes the float to rise upward against the entrance port seat to again stop flow through the valve.

In the recumbent position, the antisiphoning valve orients as seen in FIG. 3. Generally, the float rises to the ceiling 35 of the cavity which is contoured to provide at least a gentle elliptical profile with a region of high elevation distant from entrance port 36. Consequently, the float moves away from the valve seat to allow CSF to flow freely through the valve. Fluid motion produces hydrodynamic force which drags the float in the direction of fluid flow represented by the arrow in FIG. 3. While fluid flows slowly, the hydrodynamic force is small enough that the float continues to hover near the high region. The cavity size and shape are preferably selected to effectively increase the hydrodynamic force on the float when the patient experiences a sudden high flow-producing event, such as coughing or sneezing, that the float is drawn in contact with the seat 39b at exit port 38, as seen in the FIG. 4. The hydrodynamic drag on the float can be enhanced, for example, by reducing the clearance between the float and the casing and by conforming the contour of the casing closely to the shape of the float. Once the exit port is closed, high pressure maintains the float in contact with the seat. That is, the high flow-producing event increases the pressure on the cavity side of the float above the pressure on the outlet port side. Consequently, the float remains in contact with the seat until the high flow-producing event subsides. The surge might also originate in the abdomen, in which case force will move the float in the opposite direction to seal against the seat at entrance port 36, as shown in phantom in FIG. 4. Therefore, whichever direction the flow surges, the float will be forced against a seat and flow will be temporarily stopped. Finally, when the pressure driving the float against the seat is relieved, the float will move toward the ceiling of the cavity and away from the seats to reestablish flow through the valve.

The antisiphoning valve of this invention thus exhibits performance features not found on conventional valves with high density balls. First it provides a straight-through fluid flow path which enables the valve to fit within a streamlined body. Having smaller bulk, the novel antisiphoning valve will be less obtrusive under the skin than a conventional valve. It will also be less resistant to axial displacement so that the valve can more readily move with the cannulae as the patient grows. As a result, the cannulae will be subject to less tensile stress and will be less likely to accidentally disconnect. Second, the novel antisiphoning valve provides the ability to reduce or eliminate sudden CSF flow surges which could occur while the patient is in the recumbent as well as the upright position.

Figure 5:
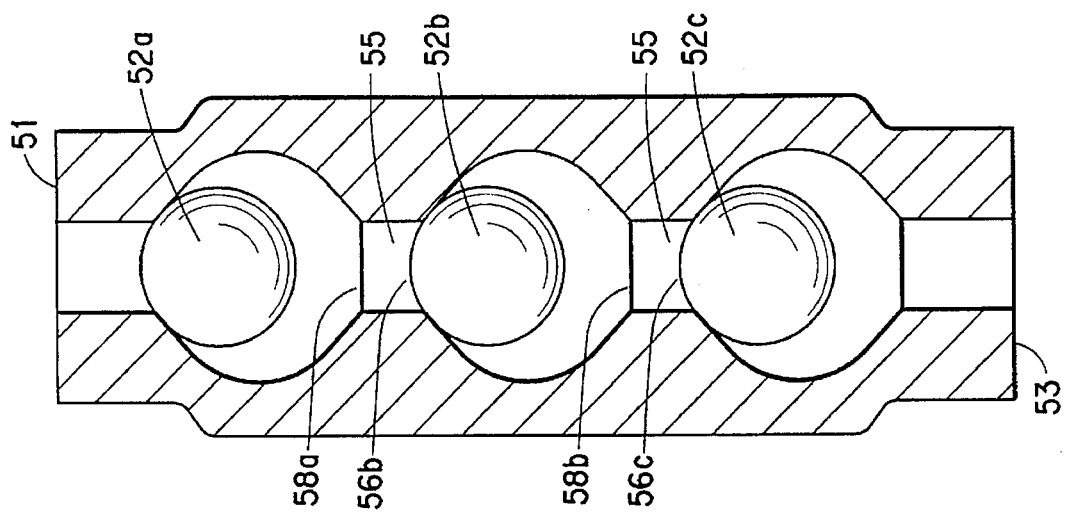
FIG. 5 is a section view of a different embodiment of an antisiphoning valve according to the present invention, wherein the valve includes a plurality of valve units.

Another embodiment of the novel antisiphoning valve is shown in FIG. 5. The internal fluid chamber of this valve includes a plurality of valve units interconnected serially between inlet port 51 and outlet port 53. Each valve unit contains a single float 52a, 52b and 52c, situated within a casing defining a elliptically contoured cross section cavity for the respective float. The units are separated by chamber sections 55 which provide room for seats for entrance ports 56b and 56c, and exit ports 58a and 58b. The float and casing of each valve unit can be the same or different sizes. The float materials can be selected to provide different buoyancies, and therefore, different threshold intracranial pressures for stopping flow.

FIG. 6 illustrates still another embodiment of the novel antisiphoning valve which includes multiple valve units. The casing of valve unit 65 is elongated so as to provide room for multiple floats 62 and 63 in the cavity. The purpose for having more than one float in a single cavity is to increase the buoyant force against the entrance port seat and thereby to increase the threshold intracranial pressure necessary to unseat the float. It is understood that the displacement of heavy fluid by the volume of a less dense float produces the buoyant force. Hence, the greater the volume of the float, the larger the displacement, and the higher the buoyant force. By providing multiple floats a high buoyant force can be obtained while maintaining smaller valve cross section dimension than might be needed for a single, spherical float.

Although the shape of the float is preferably spherical, floats of other shapes are contemplated. For example, an elongated, torpedo-shaped, float 71 can be used in an elongated valve unit casing 72, as in FIG. 7. The illustrated torpedo float has hemispherical ends 73, 74, however, frustoconical ends are also satisfactory.

The antisiphoning valve of this invention can be manufactured by well known methods. For example, with reference to FIG. 8, it is seen that the body of the novel antisiphoning valve can be constructed in two clam shell sections, 82 and 84. Starting with the sections disassembled, floats are inserted in the valve units and the sections are assembled to enclose the floats. The assembled valve is then held together with removable fasteners, such as screws 86 screwed into predrilled and tapped holes, shown in phantom. A seal between the mating surfaces can be achieved by polishing the mating surfaces to a fine tolerance finish, by constructing the body of sealably deformable plastic, such as polyolefin, polyester or polyamide plastic or copolyetherester elastomer, or by placing between the clam shell portions an elastomeric gasket 88, the thickness of which is exaggerated in the figure.

Although specific forms of the invention have been selected for illustration in the drawings, and the preceding description is drawn in specific terms for the purpose of describing these forms of the invention, this description is not intended to limit the scope of the invention which is defined in the claims.

What is claimed:

1. An antisiphoning valve for a ventriculoperitoneal shunt comprising:

a hollow body defining at least one internal fluid chamber having a chamber wall;

an outlet port on the body to connect the antisiphoning valve in fluid communication between the at least one chamber and a discharge cannula;

an inlet port on the body distant from the outlet port to connect the antisiphoning valve in fluid communication between the at least one chamber and a supply cannula;

at least one freely moving float within each chamber, the at least one freely moving float being buoyant in cerebrospinal fluid; and a first seat on the chamber wall proximate to the inlet port adapted to mate with the at least one freely moving float to stop cerebrospinal fluid flow when the antisiphoning valve in use is oriented in an upright attitude wherein the inlet port is elevated higher than the at least one chamber thereby causing cerebrospinal fluid in the chamber to buoy up the float to mate with the seat.

2. The antisiphoning valve of claim 1 further comprising a second seat on the chamber wall distant from the first seat adapted to mate with the at least one freely moving float to stop cerebrospinal fluid flow when the at least one freely moving float mates with the second seat.

3. The antisiphoning valve of claim 2 wherein the seats are frustoconical.

4. The antisiphoning valve of claim 2 wherein at least one chamber includes more than one freely moving float.

5. The antisiphoning valve of claim 2 wherein the chamber wall has a shape contoured to closely conform to the shape of the at least one freely moving float.

6. The antisiphoning valve of claim 5 wherein the at least one freely moving float is spherical and the shape of the chamber wall is oval.

7. The antisiphoning valve of claim 5 wherein the at least one freely moving float and the at least one chamber are elongated.

8. The antisiphoning valve of claim 2 wherein the hollow body defines a plurality of internal fluid chambers.

9. The antisiphoning valve of claim 8 wherein at least one chamber includes more than one freely moving float.

* * * * *

UNITED STATES PATENT AND TRADEMARK OFFICE
CERTIFICATE OF CORRECTION

PATENT NO.   :  5,634,894
DATED        :  June 3, 1997
INVENTOR(S)  :  Gary Magram It is certified that error appears in the above-identified patent and that said Letters Patent is hereby corrected as shown below:

Column 6, lines 37 and 38, replace "cerebrospinal fluid in the chamber to buoy up the float to mate with the seat" with --said at least one freely moving float to mate with the seat upon the existence of cerebrospinal fluid in the chamber--.

Signed and Sealed this

Eleventh Day of November, 1997

*Attest:*

BRUCE LEHMAN

*Attesting Officer*        *Commissioner of Patents and Trademarks*